(12) United States Patent
Wade et al.

(10) Patent No.: US 11,198,848 B2
(45) Date of Patent: *Dec. 14, 2021

(54) PROBIOTICS FOR ALTERING THE COMPOSITION OF ORAL BIOFILMS

(71) Applicants: SYMRISE AG, Holzminden (DE); PROBI AB, Lund (SE)

(72) Inventors: William Wade, Clevedon (GB); Marcus Rudolf Götz, Oberweser (DE); Manuel Pesaro, Beverungen (DE)

(73) Assignees: SYMRISE AG, Holzminden (DE); PROBI AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/070,573

(22) PCT Filed: Jan. 18, 2017

(86) PCT No.: PCT/EP2017/051011
§ 371 (c)(1),
(2) Date: Jul. 17, 2018

(87) PCT Pub. No.: WO2017/125453
PCT Pub. Date: Jul. 27, 2017

(65) Prior Publication Data
US 2019/0290705 A1    Sep. 26, 2019

(30) Foreign Application Priority Data
Jan. 19, 2016 (EP) ..................... 16151963

(51) Int. Cl.
| | | |
|---|---|---|
| *A61K 35/747* | (2015.01) | |
| *C12N 1/20* | (2006.01) | |
| *A61K 9/00* | (2006.01) | |
| *A61K 9/68* | (2006.01) | |
| *A61Q 11/00* | (2006.01) | |
| *A61K 35/00* | (2006.01) | |
| *C12R 1/225* | (2006.01) | |

(52) U.S. Cl.
CPC ............ *C12N 1/205* (2021.05); *A61K 9/0056* (2013.01); *A61K 9/0058* (2013.01); *A61K 35/747* (2013.01); *A61Q 11/00* (2013.01); *C12N 1/20* (2013.01); *A61K 2035/115* (2013.01); *C12R 2001/225* (2021.05)

(58) Field of Classification Search
None
See application file for complete search history.

(56) References Cited

U.S. PATENT DOCUMENTS

| | | | |
|---|---|---|---|
| 9,028,841 | B2 | 5/2015 | Henn et al. |
| 2008/0268006 | A1 | 10/2008 | Molin et al. |
| 2009/0208469 | A1 | 8/2009 | Alenfall et al. |
| 2010/0028449 | A1 | 2/2010 | Prakash et al. |
| 2013/0209374 | A1 | 8/2013 | Cune Castellana |
| 2014/0023620 | A1 | 1/2014 | Ioudina |
| 2014/0065218 | A1 | 3/2014 | Lang et al. |
| 2014/0199281 | A1 | 7/2014 | Henn et al. |
| 2015/0238548 | A1 | 8/2015 | Huang et al. |
| 2015/0240200 | A1 | 8/2015 | Tsai et al. |
| 2015/0250834 | A1 | 9/2015 | Tsai et al. |
| 2015/0328141 | A1 | 11/2015 | Reindl et al. |
| 2017/0306289 | A1 | 10/2017 | Chung et al. |

FOREIGN PATENT DOCUMENTS

| | | | |
|---|---|---|---|
| CN | 101190239 A | | 6/2008 |
| CN | 101703179 A | | 5/2010 |
| CN | 101715908 A | | 6/2010 |
| CN | 102470151 A | * | 5/2012 |
| CN | 102470151 A | | 5/2012 |
| CN | 104814983 A | | 8/2015 |
| EP | 1634948 A1 | | 3/2006 |
| EP | 1955702 A1 | | 8/2008 |
| EP | 2364712 A1 | | 9/2011 |
| EP | 2420580 A1 | | 2/2012 |
| EP | 3405563 B1 | | 1/2020 |
| JP | 2014000039 A | | 1/2014 |
| JP | 6538286 B2 | | 7/2019 |
| KR | 10-2012-0035923 A | | 4/2012 |
| WO | 0078322 A2 | | 12/2000 |

(Continued)

OTHER PUBLICATIONS

Anonymous: "Biogrowing—comprehensive probiotic solutions provider," 2015, pp. 1-17.
International Search Report and Written Opinion dated Oct. 17, 2019, for corresponding PCT Application No. PCT/EP2019/067007.
International Search Report and Written Opinion dated Mar. 10, 2017 for corresponding PCT Application No. PCT/EP2017/051011.
Chinese Office Action dated Jan. 11, 2019 for corresponding Chinese Patent Application No. 201780007278.3.
"Biogrowing—Comprehensive Probiotic Solutions Provider", 2015, pp. 1-16 www.biogrowing.com; XP-002759385.
Chinese Office Action dated Apr. 3, 2019 for corresponding Chinese Application No. 201780007278.3.

(Continued)

*Primary Examiner* — Allison M Fox
*Assistant Examiner* — Qing Xu
(74) *Attorney, Agent, or Firm* — Polsinelli PC

(57) ABSTRACT

The present invention relates to a certain microorganism for altering the composition of oral biofilms, in particular for use in the treatment and/or prevention of dental caries and/or periodontal disease.
In particular, the present invention relates to a microorganism for use as a probiotic agent for altering the bacterial composition of oral biofilms derived from saliva, preferably for reducing the proportions of Gram-negative anaerobic genera and/or increasing the proportions of aerobic or facultatively anaerobic genera.
Furthermore, the present invention provides oral pharmaceutical compositions, oral care products or products for nutrition or pleasure comprising the microorganism as probiotic agents as well as a method of production thereof.

17 Claims, No Drawings

(56) References Cited

FOREIGN PATENT DOCUMENTS

| | | | |
|---|---|---|---|
| WO | 2010077795 A2 | | 7/2010 |
| WO | 2010099824 A1 | | 9/2010 |
| WO | 2012022773 A1 | | 2/2012 |
| WO | 2012033151 A1 | | 3/2012 |
| WO | 2010064373 A1 | | 5/2012 |
| WO | 2012156491 A1 | | 11/2012 |
| WO | WO 2012/156491 A | * | 11/2012 |
| WO | 2014140080 A1 | | 9/2014 |
| WO | 2017035412 A1 | | 3/2017 |
| WO | 2017125447 A1 | | 7/2017 |
| WO | 2017125453 A1 | | 7/2017 |

OTHER PUBLICATIONS

Kistler, James O. et al.; "Development and pyrosequencing analysis of an in-vitro oral biofilm model," BMC Microbiology; 2015, pp. 1-10.
Anonymous: "Biogrowing—comprehensive probiotic solutions provider," 2015, XP002759385, pp. 1-16.
Sookkhee, S. et al., "Lactic acid bacteria from healthy oral cavity of Thai volunteers: Inhibition of oral pathogens," Journal of Applied Microbiology, vol. 90, No. 2, 2001, pp. 172-179.
Vuotto, Claudia et al., "Probiotics to counteract biofilm-associated infections: promising and conflicting data," International Journal of Oral Science, vol. 6, No. 4, 2014, pp. 189-194.
Chuang, Li-Chuan et al., "Probiotic effect on cariogenic bacterial flora," Clinical Oral Investigations, vol. 15, No. 4, 2010, pp. 471-476.
Iqbal, S. et al., "β-Galactosidase from *Lactobacillus plantarum* WCFS1: biochemical characterization and formation of prebiotic galacto-oligosaccharides," Carbohydrate Research, vol. 345, 2010, pp. 1408-1416.
International Search Report and Written Opinion dated Mar. 16, 2018, for corresponding PCT Application No. PCT/EP2018/051112.
Snel, J. et al., "Competitive Selection of Lactic Acid Bacteria That Persists in the Human Oral Cavity", Applied and Environmental Microbiology, vol. 77, No. 23, 2011, pp. 8445-8450 XP055379435.
Roy, Byun et al., "Quantitative analysis of diverse *Lactobacillus* species present in advanced dental caries", Journal of Clinical Microbiology, American Society of Microbiology, vol. 42, No. 7, 2004, pp. 3128-3136 XP002488329.
Azcarate-Peril, M. A. et al., "Analysis of the Genome Sequence of *Lactobacillus gasseri* ATCC 33323 Reveals the Molecular Basis of an Autochthonous Intestinal Organism", Applied and Environmental Microbiology, vol. 74, No. 15, 2008, pp. 4610-4625 XP055029769.
International Preliminary Report on Patentability dated Jul. 24, 2018 for corresponding PCT Application No. PCT/EP2017/051011.
International Search Report and Written Opinion dated Mar. 17, 2017 in corresponding PCT Application No. PCT/EP2017/051005.
Li, Allen, "Biogrowing probiotics brochure", 2015, p. 1, XP002758029.
Written Opinion dated Jul. 27, 2017 for corresponding PCT Application No. PCT/EP2017/051003.
Written Opinion dated Mar. 22, 2019 for corresponding PCT Application No. PCT/EP2018/067090.
European Office Action dated Mar. 8, 2018 for corresponding EP Application No. EP 16151963.2.
Australian Office Action dated Sep. 10, 2018 for corresponding AU Application No. 2017208481.
Office Action dated Apr. 2, 2020, for corresponding U.S. Appl. No. 16/070,553.
Biogrowing: "Dietary Supplements (Biotic Health™)," 2010 pp. 1-3 XP002758028.
European Office Action dated Mar. 12, 2021 for corresponding European Application No. 18702144.9.
Mette Kirstine Keller et al., "Co-aggregation and growth inhibition of probiotic lactobacilli and clinical isolates of mutans *streptococci:* An in vitro study," Acta Odontologica Scandinavica, vol. 69, 2011, pp. 263-268 XP009162555.
Zhihong Sun et al., "Expanding the biotechnology potential of lactobacilli through comparative genomics of 213 strains and associated genera," Nature Communications, 2015, pp. 1-13 XP002769022.
S. Resta-Lenert et al., "Live probiotics protect intestinal epithelial cells from the effects of infection with enteroinvasive *Escherichia coli* (EIEC)," Inflammatory Bowel Disease, vol. 52, 2003, pp. 988-997 XP055678154.
Tamara Smokvina et al., "*Lactobacillus paracasei* Comparative Genomics: Towards Species Pan-Genome Definition and Exploitation of Diversity," PLOS ONE, vol. 8, Issue 7, 2013, pp. 1-18 XP055711380.
C. Lang et al., "Specific Lactobacillus/Mutans *Streptococcus* Co-aggregation," Research Reports, vol. 89, No. 2, 2009, pp. 175-180 XP009162445.
Office Action dated Mar. 18, 2021 in co-pending U.S. Appl. No. 16/478,514.

* cited by examiner

PROBIOTICS FOR ALTERING THE COMPOSITION OF ORAL BIOFILMS

CROSS-REFERENCE TO RELATED APPLICATIONS

This application is a national stage application (under 35 U.S.C. § 371) of PCT/EP2017/051011, filed Jan. 18, 2017, which claims benefit of European Application No. 16151963.2, filed Jan. 19, 2016, which are incorporated herein by reference in their entireties.

The present invention relates to a certain microorganism for altering the composition of oral biofilms, in particular for use in the treatment and/or prevention of dental caries and/or periodontal disease.

In particular, the present invention relates to a microorganism for use as a probiotic agent for altering the bacterial composition of oral biofilms derived from the teeth, preferably for reducing the proportions of Gram-negative anaerobic genera and/or increasing the proportions of aerobic or facultatively anaerobic genera.

Furthermore, the present invention provides oral pharmaceutical compositions, oral care products or products for nutrition or pleasure comprising the microorganism as probiotic agent as well as a method of production thereof.

Inflammatory conditions of the gums are primarily induced by the formation of dental plaque. Colonizing bacteria form a biofilm on the surface of the teeth aided by the presence of food residues as well as components of saliva. If not sufficiently cleared away at an early stage, plaque films on the surface of the teeth result in deposition of dental calculus which is very hard to remove. The presence of raised numbers of bacteria at the gingival margin leads to inflammation of the gingivae, known as gingivits. In susceptible individuals, gingivitis may progress to periodontitis, which can lead to tooth loss. In particular, lipopolysaccharides (LPS) present in Gram-negative bacteria can cause a nonspecific immune response by LPS-stimulated macrophages, which release prostaglandin E2 (PEG2) and pro-inflammatory mediators such as interleukins and TNF-α in the affected tissue. The pro-inflammatory mediators induce the release of further PGE2s and matrix metalloproteinases (MMPs) from the residing fibroblasts, which destroy the extracellular matrix of the surrounding tissue. This allows bacteria to penetrate deeper into the tissue and promote the inflammatory process independent of the outer layer of the epithelium and the dental root causing the formation of a periodontal pocket. The alveolar bone supporting the tooth resorbs ahead of the advancing bacteria and, causing the tooth to become unstable and, if left untreated, lost.

Many different approaches have addressed this problem, ranging from improved methods for the mechanical removal of plaque and dental calculus to the use of oral care products with strong anti-bacterial properties.

However, not all the bacteria present in the oral cavity are associated with disease and many even promote oral health. Therefore, it is desirable to establish a balance towards a healthy composition of the mouth flora instead of unspecifically eradicating resident bacteria.

Probiotic action of bacteria in the oral cavity has been subject to some research but it has been found to vary strongly with the species and suitable parameters for efficient application are hard to establish because the action may rely on largely unrelated effects.

Among the probiotic actions, general anti-bacterial effects against disease-associated species, the reduction or prevention of bacterial adhesion to the surface of the teeth as well as anti-inflammatory effects have been discussed in the literature.

WO 2010/077795 A2 relates to compositions to improve oral health comprising a therapeutically effective amount of beneficial bacteria selected from specific strains of streptococci and lactobacilli.

Probiotics containing teeth and oral care products are disclosed as being capable of preventing parodontits and gingivitis according to DE 20 2009 011 370 U1, which recites a large variety of probiotic bacteria including lactobacilli, bifidobacteria, enterococci, sporolactobacilli and streptococci. Specific strains are not mentioned, however, and the alleged probiotic action is not further evaluated.

WO 2010/008879 A2 provides a confectionary composition containing an inactive probiotic, which is activable upon contact with water. As probiotics, different strains of lactobacilli and bifidobacteria are disclosed. Probiotic effects mentioned in WO 2010/008879 A2 include the reduction of gum inflammation for example by suppressing pathogenic bacteria.

EP 1 852 122 A1 relates to dental and gingival health compositions containing dehydrated, reactivable microorganisms. It is explained that the microorganisms may combat virulent pathogenic bacterial flora by re-establishing the equilibirium of the affected tissue due to competition. WO 2005018342 also refers to a competition effect where probiotic bacteria are able to inhibit colonization or out growth of a pathogen by competing for nutrients or attachment sites.

Furthermore, it has been established, that, besides a mere competitive displacement, probiotic bacteria may be capable to form co-aggregates with disease-associated species which are easily flushed out and reducing the load of disease-associated species in the mouth.

The use of exogenous lactic bacteria for prophylaxis or treatment of dental caries, dental plaque and periodontal infection is disclosed in WO 00/09080. Colonization via specific binding to resident microflora (co-aggregation) is mentioned but the use of probiotics according to WO 00/09080 relies on the effect that certain lactic bacteria, which are not part of resident microflora, are capable of adhering directly to the pellicle of the teeth thus displace pathogens or prevent their attachment.

The ability of probiotic bacteria to replace pathogens or form aggregates interfering with pathogen biofilm formation is mentioned in WO 2012/022773 A1. WO 2012/022773 A1, is primarily concerned with probiotic compositions for oral health comprising effective amounts of *Lactobacillus plantarum* CECT 7481 and *Lactobacillus brevis* CECT 7480, which are demonstrated to have anti-bacterial properties against certain pathogens.

WO 2012028759 (EP 2 612 904 A2) provides anti-microbial bacterial strains of the genus *streptococcus* for use in treatment of infectious disease in the oral cavity, which is based on the formation of co-aggregates of *S. mutans* with the probiotic strains.

WO 2012/100991 discloses the use of binder organisms (lactic acid bacteria) to bind streptococci in the oral cavity, which are then flushed out thus preventing colonization by the pathogens and the formation of caries. Effective binder organisms according to WO 2012/100991, are certain strains of *Lactobacillus paracasei* and *Lactobacillus rhamnosus*.

In summary, it has been demonstrated that certain strains belonging to the genus *Lactobacillus* and other genera are antagonistic to some oral disease-associated bacterial species in in-vitro assays [1]. These strains have the potential to be used as probiotics for prevention and therapy of dental caries and periodontal disease. However, assays used to demonstrate microbial antagonism are performed singly on agar media and are therefore rather artificial. This is because oral bacteria naturally form biofilms that are composed of many different species, not all of which have been cultivated [2,3]. Deep sequencing studies have, for example, detected hundreds of species in dental plaque samples from individual subjects [4-6]. Whilst some in-vitro oral biofilm assays have been developed and used for testing oral care products, these have typically used relatively simple defined bacterial inocula resulting in biofilms with a low complexity [7-9]. Given the high richness and diversity of oral biofilms, it would be preferable to use natural diverse oral inocula, such as saliva or dental plaque, in order to more accurately represent the in-vivo ecosystem.

One in-vitro system that has been previously developed and used to grow bacteria as biofilms is the Calgary Biofilm device (CBD) [10]. In this system, biofilms are grown on pegs protruding from the lid of a 96-well plate. The pegs are immersed in a growth medium that can easily be replaced by transferring the lid to a new baseplate, thereby enabling the long-term growth of biofilms. The CBD was originally developed to determine the susceptibility of bacterial biofilms to antibiotics for applications such as medical device-related infections, and is therefore commercially available as the 'Minimum Biofilm Eradication Concentration' (MBEC) assay (Innovotech, Canada). Previous work has demonstrated that uniform biofilms with reproducible total viable counts can be obtained when using simple defined bacterial inocula [11]. In addition, an oral microbial biofilm model has been developed using the CBD seeded with the saliva of healthy individuals as a natural inoculums [12]. The pegs of the CBD were coated in hydroxyapatite to provide a surface chemically similar to tooth enamel. The use of next generation sequencing allowed a comprehensive characterisation of the bacterial composition of the biofilms. The biofilms were shown to be complex but reproducible, thus accurately representing the in-vivo conditions of the oral cavity.

The effect of *Lactobacillus reuteri* probiotic strains on the composition of in-vitro oral biofilms derived from saliva has been previously investigated in a study using hydroxyapatite discs and constant depth film fermenters (CDFFs) [13]. Introduction of the live strains, both to developing and mature biofilms, altered the composition of the biofilms compared to a control. The differences were most pronounced in developing biofilms in which significantly increased numbers of total anaerobes, Gram-negative anaerobes and streptococci were detected. However, dosing of mature biofilms resulted in reductions in total anaerobes and streptococci but increases in facultative and anaerobic Gram-negative anaerobes. The authors also showed that the *L. reuteri* strains could persist in the mature biofilms after dosing ceased.

Using a CBD model, it was now possible for the first time to individually assess the impact of treatment with a large number of bacterial strains on the composition of complex oral biofilms and thus allow a specific selection of strain with the most efficient beneficial effect on the balance towards a healthy biofilm composition on the surface of teeth. Notably, it has been found out, that certain strains are capable to reduce the proportion of disease-associated bacteria while increasing the proportion of bacteria, which are beneficial for oral health.

An object of the present invention was to provide a microorganism which can be used in highly effective treatment and/or prevention of periodontal disease.

A further object of the present invention was to provide a microorganism which is capable to balance the bacterial composition of oral biofilms derived from saliva in favor of bacteria beneficial for oral health.

Furthermore, it was an object of the present invention to provide compositions and products to effectively use the microorganism of the present invention in oral care.

The objective of the present invention is met by a microorganism for use in the treatment and/or prevention of dental caries and/or periodontal disease, wherein the microorganism is *Lactobacillus paracasei* LPc-G110 (CCTCC M 2013691).

The extensive screenings leading up to the present invention revealed that *Lactobacillus paracasei* LPc-G110 (CCTCC M 2013691) impacted the community composition of the biofilms. At the genus level, many of the taxa that were lower in proportion in the *Lactobacillus paracasei* LPc-G110 (CCTCC M 2013691)-treated biofilms were Gram-negative anaerobic genera, including un-named genera within the phylum Bacteroidetes, *Fusobacterium, Prevotella*, and Pyramidobacter. Reductions in the proportions of Gram-negative anaerobes advantageously helps to maintain periodontal health as these taxa have been associated with the onset of gingivitis in studies of experimental gingivitis [6, 28, 29]. In contrast, a number of the genera that were increased relative to the negative control were aerobic/facultatively anaerobic genera including *Corynebacterium* and *Neisseria* and are common in early immature plaque typical of gingival health [6, 30]. At the species level, *Fusobacterium nucleatum* was significantly lower in relative abundance in biofilms treated with heat-attenuated *Lactobacillus paracasei* LPc-G110 (CCTCC M 2013691). *Fusobacterium nucleatum* was previously associated with gingivitis [6, 29] and has been described as a 'bridging' organism in plaque through its ability to coaggregate with both early and late colonisers [31].

The strain *Lactobacillus paracasei* LPc-G110 has been deposited under the Budapest Treaty at the China Center for Type Culture Collection (CCTCC), Wuhan University, Wuhan 430072, China, under the accession number CCTCC M 2013691 (by BioGrowing Co., Ltd., No. 10666 Songze Rd., Qingpu Shanghai 201700, China) on 23 Dec. 2013.

In a preferred embodiment of the present invention the microorganism described above is an attenuated or a dead microorganism, preferably a heat-attenuated microorganism.

In the studies described below, it has been demonstrated that the microorganism according to the invention is particularly efficient in a heat-attenuated state.

The activity of the heat-attenuated strain in the present study may be due to the release of bioactive molecules during the heat treatment, and these may have some specificity against certain oral species.

In one aspect, the present invention relates to the microorganism recited above for use as a probiotic agent for altering the bacterial composition of oral biofilms derived from saliva, preferably for reducing the proportions of Gram-negative anaerobic genera and/or increasing the proportions of aerobic or facultatively anaerobic genera, preferably in each case with respect to a negative control (cf. below, example 1).

In a preferred embodiment, the microorganism according to the invention is for reducing the proportions of one or more bacteria selected from the group consisting of Bacteroidetes, *Fusobacterium, Prevotella* and Pyramidobacter and/or for increasing the proportions of *Corynebacterium* and/or *Neisseria*, preferably in each case with respect to a negative control (cf. below, example 1).

As explained above, the microorganism according to the invention tips the microbial balance in biofilms towards an accumulation of beneficial microorganisms while the proportion of detrimental bacteria is reduced. In particular, the Gram-negative anaerobic genera, especially Bacteroidetes, *Fusobacterium, Prevotella* and Pyramidobacter have been associated with the onset of gingivitits and are advantageously reduced in proportion by the microorganism according to the invention in oral biofilm compositions. On the other hand, aerobic or facultatively anaerobic genera, in particular *Corynebacterium* and *Neisseria*, which are common in early immature plaque typical of periodontal health, are increased in proportion by the microorganism according to the invention, thus optimizing the beneficial effect.

A further aspect of the present invention relates to an oral pharmaceutical composition, oral care product or product for nutrition or pleasure, comprising *Lactobacillus paracasei* LPc-G110 (CCTCC M 2013691), wherein the total amount of *Lactobacillus paracasei* LPc-G110 (CCTCC M 2013691) is sufficient for treating and/or preventing dental caries and/or periodontal disease, further preferably wherein the total amount of *Lactobacillus paracasei* LPc-G110 (CCTCC M 2013691) is in the range from 0.01 to 100%, more preferably in the range from 0.1 to 50%, most preferably in the range from 1 to 10%, in each case with respect to the total weight of the composition, and/or wherein the total amount of *Lactobacillus paracasei* LPc-G110 (CCTCC M 2013691) is in the range from $1 \times 10^3$ to $1 \times 10^{11}$ colony forming units (CFU), more preferably in the range from $1 \times 10^5$ to $1 \times 10^{10}$ CFU.

In order to provide compositions and products to practically use the microorganism of the present invention in oral care, a composition is provided comprising effective amounts of the microorganism according to the invention. In particular, the amounts specified above have been demonstrated to be suitable for achieving the inventive effect.

Furthermore, the present invention relates to a composition or product as described above for use in the treatment and/or prevention of dental caries and/or periodontal disease, preferably for altering the bacterial composition of oral biofilms derived from saliva.

Preferably, the composition or product is used for reducing the proportions of Gram-negative anaerobic genera and/or increasing the proportions of aerobic or facultatively anaerobic genera, in each case with respect to a negative control.

Particularly preferably, the composition or product is used for reducing the proportions of one or more bacteria selected from the group consisting of Bacteroidetes, *Fusobacterium, Prevotella* and Pyramidobacter and/or for increasing the proportions of *Corynebacterium* and/or *Neisseria*, preferably in each case with respect to a negative control (cf. below, example 1).

A composition according to the invention may further comprise one or more components selected from the group consisting of carriers, excipients or further active ingredients such as, for example, active agents from the group of non-steroidal antiphlogistics, antibiotics, steroids, anti-TNF-alpha antibodies or other biotechnologically produced active agents and/or substances as well as analgetics, dexpanthenol, prednisolon, polyvidon iodide, chlorhexidine-bis-D-gluconate, hexetidine, benzydamine HCl, lidocaine, benzocaine, macrogol lauryl ether, benzocaine in combination with cetidyl pyridinium chloride or macrogol lauryl ether in combination with protein free hemodialysate from calf blood, as well as for example fillers (e.g. cellulose, calcium carbonate), plasticizer or flow improves (e.g. talcum, magnesium stearate), coatings (e.g. polyvinyl acetate phtalate, hydroxyl propyl methyl cellulose phtalate), disintegrants (e.g. starch, cross-linking polyvinyl pyrrolidone), softener (e.g. triethyl citrate, dibutyl phthalate) substances for granulation (lactose, gelatin), retardation (e.g. poly (meth)acrylic acid methyl/ethyl/2-trimethyl aminomethyl ester copolymerizates in dispersion, vinyl acetate/crotonic acid copolymerizates), compaction (e.g. microcrystalline cellulose, lactose), solvents, suspending or dispersing agents (e.g. water, ethanol), emulsifiers (e.g. cetyl alcohol, lecithin), substances for modifying the rheological properties (silica, sodium alginate), substances for microbial stabilization (e.g. benzalkonium chloride, potassium sorbate), preservatives and antioxidants (e.g. DL-alpha-tocopherol, ascorbic acid) substances for modifying pH (lactic acid, citric acid), blowing agents or inert gases (e.g. fluorinated chlorinated hydrocarbons, carbon dioxide), dyes (iron oxide, titanium oxide), basic ingredients for ointment (e.g. paraffines, bees wax) and others as described in the literature (e.g. in Schmidt, Christin. Wirk- und Hilfsstoffe für Rezeptur, Defektur und Großherstellung. 1999; Wissenschaftliche Verlagsgesellschaft mbH Stuttgart oder Bauer, Frömming Führer. Lehrbuch der Pharmazeutischen Technologie. 8. Auflage, 2006. Wissenschaftliche Verlagsgesellschaft mbH Stuttgart).

A composition or product according to the present invention may also be coated or encapsulated.

Encapsulation of a composition according to the invention may have the advantage of allowing a controlled release, for example upon contact with water, or a continuous release over an extended period of time. Moreover, the composition may be protected from degradation improving the shelf life of the product. Methods for encapsulation of active ingredients are well known in the art and a number of encapsulation materials as well as methods how to apply them to a composition according to specific requirements are available.

Furthermore, a composition or product according to the invention may be in the form of a solution, suspension, emulsion, tablets, granules, powder or capsules.

The composition or product according to the invention may be selected form the group consisting of toothpaste, tooth gel, tooth powder, tooth cleaning liquid, tooth cleaning foam, mouth wash, mouth spray, dental floss, chewing gum and lozenges.

Such compositions or products may contain abrasive systems (abrasive and/or polishing components) such as silicates, calcium carbonate, calcium phosphate, aluminum oxide and/or hydroxyl apatite, surfactants such as e.g. sodium lauryl sulfate, sodium lauryl sarcosinate and/or cocamidopropyl betaine, humectants such as glycerol and/or sorbitol, thickening agents, e.g. carboxy methyl cellulose, poly ethylene glycols, carrageenans and/or Laponite®, sweeteners such as saccharine, aroma and taste correcting agents for unpleasant taste impressions, taste modifying substances (e.g. inositol phosphate, nucleotides, e.g. guanosine monophosphate, adenosine monophosphate or other substances, e.g. sodium glutamate or 2-phenoxy propionic acid), cooling agents such as menthol derivates (e.g. L-mentyl lactate, L-menthyl alkyl carbonate, menthone ketals), icilin and icilin derivates, stabilizers and active agents such as sodium fluoride, sodium monofluoro phosphate, tin difluoride, quarternary ammonium fluorides, zinc citrate, zinc sulfate, tin pyrophosphate, tin dichloride, mixtures of different pyrophosphates, triclosane, cetyl pyridinium chloride, aluminum lactate, potassium citrate, potassium nitrate, potassium chloride, strontium chloride, hydrogen peroxide, aroma substances, sodium bicarbonate and/or smell correcting agents.

Chewing gums or dental care chewing gums may comprise a chewing gum base comprising elastomers, e.g. polyvinyl acetate (PVA), polyethylene, (low or medium molecular) polyiso butane (PIB), polybutadiene, isobutene/isoprene copolymers, polyvinyl ethyl ether (PVE), polyvinyl butyl ether, copolymers of vinyl esters and vinyl ethers, styrene/butadiene copolymers (SBR) or vinyl elastomers, e.g. based on vinyl acetate/vinyl laurate, vinyl acetate/vinyl stearate or ethylene/vinyl acetate and mixtures of the mentioned elastomers as e.g. example described EP 0 242 325, U.S. Pat. No. 4,518,615, 5,093,136, 5,266,336, 5,601,858 or 6,986,709. Additionally chewing gum bases may contain further ingredients, e.g. (mineral) filers, e.g. calcium carbonate, titanium dioxide, silicone dioxide, talcum, aluminum oxide, dicalcium phosphate, tricalcium phosphate, magnesium hydroxide and mixtures thereof, plasticisers (e.g. lanolin, stearic acid, sodium stearate, ethyl acetate, diacetin (glycerol diacetate), triacetin (glycerol triacetate) and trietyhl citrate), emulsifiers (e.g. phosphatides, such as lecithin and mono and diglycerides of fatty acids, e.g. glycerol monostearate), antioxidants, waxes (e.g. paraffine waxes, candelilla waxes, carnauba waxes, microcrystalline waxes and polyethylene waxes), fats or fatty oils (e.g. hardened (hydrogenated) plant or animal fats) and mono, di or triglycerides.

Finally, the present invention also relates to a method of producing an oral pharmaceutical composition, an oral care product or a product for nutrition or pleasure as described above, comprising the following step:
combining *Lactobacillus paracasei* LPc-G110 to one or more further components, preferably to one or more components selected form the group consisting of carriers, excipients or further active ingredients.

The following examples are added to illustrate the present invention without being intended to limit the scope.

EXAMPLE 1: SCREENING OF BACTERIAL STRAINS FOR EFFECTS ON THE COMPOSITION OF COMPLEX IN-VITRO ORAL BIOFILMS

The screening was performed on a number of candidate probiotic strains of *Lactobacillus casei*, *Lactobacillus plantarum*, *Lactobacillus rhamnosus*, *Lactobacillus paracasei*, *Lactobacillus bulgaricus* and *Lactobacillus fermentum*
Sample Collection Five millilitres of saliva were obtained from the participants by expectoration into sterile universal tubes. Saliva was placed on ice and used for inoculation within an hour of collection. The samples were pooled in equal volumes for the inoculation of the CBD plates.
Inoculation of the Calgary Biofilm Device and Incubation of Biofilms The pooled saliva was vortexed for 15 s and 200 µl was pipetted per well in 96-well microplates, up to the required number of wells. Wells around the outside of the microplates were not used. The CBD lids with pegs were fitted onto the microplates so that the hydroxyapatite-coated pegs were bathed in the saliva. The CBD plates were then incubated at 37° C. in air+5% $CO_2$ for 18 hours, after which the lids were transferred to new baseplates containing 200 µl of pre-reduced Brain Heart Infusion (BHI) broth (Fluka Analytical) growth medium supplemented with hog gastric mucin (1 g/L), haemin (10 mg/L), and vitamin K (0.5 mg/L). The pegs were incubated in air+5% $CO_2$ for 14 days and the growth medium was changed every 3.5 days.
Treatment of Biofilms After seven days of growth, the biofilms were treated twice daily with live or heat-attenuated probiotic strains at a concentration of $1\times10^8$ CFUs/ml suspended in BHI, a negative control (sterile BHI), or a positive control (0.1% v/v thymol), for seven days. Heat-attenuation of probiotic strains was performed by placing the bacterial suspension(s) in a Techne heating block at 80° C. for 30 mins. After the incubation, the suspensions were placed on ice for 5 mins and then stored at −70° C. until required. The live probiotic preparations were stored at −70° C. until required and were resuscitated before use by incubating them on a heating block at 37° C. for 30 minutes.

Treatments were carried out at 9 am and 5 pm each day. Two hundred microliter aliquots of each probiotic preparation or control were pipetted into the appropriate wells of a 96-well microplate for the treatment procedure. Three sample replicates of three pegs (total of nine pegs) were treated per probiotic preparation. Pegs with biofilms were immersed into the probiotic preparations or controls by transferring the lid of the CBD to the microplate containing the treatments. The exposure was carried out on a shaker, with gentle agitation, for 1 minute. The pegs were then washed by briefly immersing them into PBS on a shaker for 30 seconds, before returning them to the growth medium.
Removal of Pegs and Propidium Monoazide Treatment of Samples for Pyrosequencinq Analysis At 14 days, pegs with biofilms were snapped off the lid with sterile pliers and washed by dipping into sterile PBS three times. All of the visible biofilm material was then removed using a sterile curette and suspended into 500 µl of PBS. The material from three pegs was pooled to produce one sample for analysis, and three samples were processed for each treatment group. Each sample was subjected to propidium monoazide (PMA) treatment to prevent subsequent PCR amplification of extracellular DNA and DNA from dead or damaged cells [14]: 1.25 µl of PMA was added (at a final concentration of 50 µM) to the cells suspended in PBS and incubated in the dark with occasional shaking for 5 mins at room temperature. The samples were then exposed to light from a 500 W halogen lamp for 5 mins at a distance of 20 cm in order to form a covalent linkage between the PMA and the DNA. During the exposure time the samples were placed on ice to avoid excessive heating and subjected to occasional shaking. The samples were used for DNA extractions immediately after the PMA treatment.
DNA Extraction DNA was extracted from the pooled saliva and the biofilm samples using the GenElute Bacterial DNA extraction kit (Sigma-Aldrich). DNA extraction was performed following the manufacturer's instructions with an additional cell lysis step to increase the recovery of DNA from Gram-positive cells, in which samples were incubated in a 45 mg/ml lysozyme solution at 37° C. for 30 mins.
Pyrosequencing of 16S rRNA Genes The bacterial composition of the biofilms and saliva was determined using 454 pyrosequencing of partial 16S rRNA genes as described previously [6], with some minor modifications. PCR amplification of a fragment of the 16S rRNA gene, approximately 500 bp in length covering the V1-V3 hypervariable regions, was performed for each DNA sample using composite fusion primers. The fusion primers comprised the broad-range 16S rRNA gene primers 27 FYM [15] and 519 R [16] along with Roche GS-FLX Titanium Series adapter sequences (A and B) for 454-pyrosequencing using the Lib-L emulsion-PCR method. The forward primers included previously described 12-base error-correcting Golay barcodes. PCR reactions were performed using Extensor Hi-fidelity PCR mastermix (Thermo-Scientific) along with the appropriate barcoded forward primer and the reverse primer. The PCR conditions were as follows: 5 mins initial denaturation at 95° C., followed by 25 cycles of 95° C. for 45 s, 53° C. for 45 s and 72° C. for 45 s and a final extension of 72° C. for 5 mins. PCR amplicons were then purified using the QIAquick PCR purification kit (Qiagen) according to the manufacturer's instructions. The size and purity of the amplicons was checked using the Agilent DNA 1000 kit and the Agilent 2100 Bioanalyzer. Quantitation of the amplicons was performed by means of a fluorometric assay using the Quant-iT Picogreen fluorescent nucleic acid stain (Invitrogen). The amplicons were then pooled together at equimolar concentrations ($1 \times 10^9$ molecules/µl). Emulsion-PCR and unidirectional sequencing of the samples was performed using the Lib-L kit and the Roche 454 GS-FLX+ Titanium series sequencer by the Department of Biochemistry, Cambridge University, Cambridge, UK.

Sequence Analysis

Sequence analysis was performed using the 'mothur' software suite version 1.34 [17], following the 454 standard operating procedure [18] on mothur.org. The sequences were denoised using the AmpliconNoise algorithm [19], as implemented by mothur. Sequences that were less than 400 bases in length and/or had one of the following: >2 mismatches to the primer, >1 mismatch to the barcode regions, and homopolymers of >8 bases in length, were discarded. The remaining sequences were trimmed to remove primers and barcodes and aligned to the SILVA 16S rRNA reference alignment [20]. The UChime algorithm [21] was used to identify chimeric sequences, which were then removed from the dataset. Sequences were clustered into operational taxonomic units (OTUs) at a genetic distance of 0.015 (approximately species level) using the average neighbour algorithm and identified using a Naïve Bayesian classifier [22] with the Human Oral Microbiome Database (HOMD) reference set (version 13).

Statistical Analysis

The sequences for each sample were randomly sub-sampled to the same number (that of the sample with the lowest number of sequences) for statistical OTU-based diversity comparisons. The extent of sampling of the communities was assessed using Good's non-parametric coverage estimator [23]. The diversity of the communities was calculated using Simpson's inverse diversity index [24]. The community structure of the samples/treatment groups was compared using distance matrices generated with the thetaYC calculator [25]. The distance matrices were visualised using non-metric multidimensional scaling (NMDS) plots generated in R (r-project.org). Analysis of molecular variance (AMOVA) [26], as implemented in mothur, was used to determine if there were statistically significant differences between treatments groups based on the thetaYC distance matrix. Heat maps and dendrograms based on the proportions of bacterial genera were generated in R using the 'vegan' package. The dendrograms were based on the 'Bray-Curtis' index of dissimilarity in community structure as implemented by the vegan package. Linear Discriminant Analysis Effect Size (LEfSe) [27] analysis was used to detect species-level OTUs that were significantly differentially abundant between the negative control biofilms and treatment groups.

Results

The replicate that amplified successfully was from the positive control treatments of the heat-attenuated treatment experiment. A total of 468,261 16S rDNA sequences were obtained, with a mean length of 427 bases, for analysis after filtering and removal of sequence chimeras. The mean number of species-level OTUs detected in the biofilm samples was 213.3 (±24.7) and 284 (±1.4) in the pooled saliva inocula.

Comparisons of the biofilms treated with heat-attenuated probiotic strains and the negative control biofilms in a non-metric multidimensional scaling (NMDS) plot did not indicate marked differences in bacterial community structure (thetaYC calculator based on the relative abundances of all the OTUs present in the communities) in most cases. However, the treatment with *L. paracasei* LPc-G110, did show a difference to the negative control, which was indicated by a shift along the NMDS axes away from the control. The single thymol positive control replicate sample showed the greatest dissimilarity to the negative control. Analysis of molecular variance (AMOVA) showed that there was an overall significant difference among the different treatment groups (P<0.001), although differences between individual treatments and the negative control were not statistically significant.

Comparisons of the composition of the biofilms using dendrograms and heat maps based on the relative abundances of the different genera, supported the findings of the OTU analyses. For the heat-attenuated treatments, two of the three *L. paracasei* LPcG110 replicates clustered separately from the remaining biofilms. The heat map indicated that these differences were principally due to reductions in the relative abundances of Bacteroidetes, *Fusobacterium*, *Prevotella* and Pyramidobacter, and increases in *Corynebacterium* and *Neisseria*. In addition, the thymol-treated biofilm showed a marked difference to the other biofilms and negative control biofilms, and was principally comprised of *Corynebacterium*, *Neisseria* and *Streptococcus*.

Statistical analysis using Linear Discriminant Analysis Effect Size (LEfSe) indicated that 37 species-level OTUs were significantly differentially abundant between *L. paracasei* LPc-G110 and the negative control.

EXAMPLE 2: PROBIOTIC LOZENGE OR COMPRIMATE

| No | Block | Ingredients | Isomalt Comprimates | | |
|---|---|---|---|---|---|
| | | | Placebo | Probiotic only | +Flavor |
| 1 | A | Magnesium Stearate | 1.800% | 1.800% | 1.800% |
| 2 | | Acesulfam | 0.050% | 0.050% | 0.050% |
| 3 | | Sucralose | 0.025% | 0.025% | 0.025% |
| 4 | | Probiotic Material | | 1.000% | 1.000% |
| 5 | | Flavor (e.g. 134229 Optamint Peppermint s/d) | | | 0.500% |
| 6 | B | Isomalt | 98.125% | 97.125% | 96.625% |
| | | Sum total | 100.00% | 100.00% | 100.00% |

Production Method:
  components 1 and 6 are dried in a vacuum compartment drier at 50° C. and a pressure of max. 10 mbar for 16 hours
  all components are weight out exactly components 1, 2, 3, 4 and 5 combined and thoroughly mixed (block A). The probiotic material is applied in lyophilized form having an activity of about $10^5$ to $10^{12}$ colony forming units (CFU) per gram.
  block A is subsequently added to component 6 and mixed thoroughly for 5 minutes
  the powder mixture is pressed into tablets in a tablet press EK0 (Korsch AG, Berlin) at an adjusted pressure of 15-20 kN target parameters:
    tablet diameter: 20 mm
    tablet weight: 2.0 g
  storage at RT in sealed aluminum sachets. Per 5 lozenges 1 g of desiccant is used for dehumidification (activated by 3 h storage at 105° C. in a vacuum compartment drier)

EXAMPLE 3: POWDER DENTIFRICE

| | | | | Toothpowder | |
|---|---|---|---|---|---|
| No | Block | Ingredients | Placebo | Probiotic only | +Flavor |
| 1 | A | Magnesium Carbonate | 3.00% | 3.00% | 3.00% |
| 2 | | Sodium Bicarbonate | 2.00% | 2.00% | 2.00% |
| 3 | | Sodium Fluoride | 0.25% | 0.25% | 0.25% |
| 4 | | Sodium Saccharin | 0.60% | 0.60% | 0.60% |
| 5 | B | Probiotic Material | | 4.00% | 4.00% |
| 6 | | Flavor (e.g. 134229 Optamint Peppermint s/d) | | | 2.00% |
| 7 | C | Calcium carbonate | 94.15% | 90.15% | 88.15% |
| | | Sum total | 100.00% | 100.00% | 100.00% |

Production Method:
  component 7 is dried in a vacuum compartment drier at 50° C. and a pressure of max. 10 mbar for 16 hours
  all components are weight out exactly
  components 1, 2, 3 and 4 are combined and thoroughly mixed together (block A)
  components 5 and 6 are, if necessary, combined and thoroughly mixed (block B). The probiotic material is applied in lyophilized form having an activity of about $10^5$ to $10^{12}$ colony forming units (CFU) per gram.
  blocks A and B are subsequently combined and thoroughly mixed together
  the mixture is added to component 7 and mixed thoroughly for 5 minutes
  the powder mixture is made up into portions of 0.5 g each storage at RT together with 1 g of desiccant per portion (activated by 3 h storage at 105° C. in a vacuum compartment drier) in sealed aluminum sachets

EXAMPLE 4: POWDER DENTIFRICE

| No | Block | Ingredients | Toothpaste tablets |
|---|---|---|---|
| 1 | A | Magnesium Carbonate | 3.00% |
| 2 | | Sodium Bicarbonate | 2.00% |
| 3 | | Sodium Fluoride | 0.25% |
| 4 | | Sodium Saccharin | 0.60% |
| 5 | | Sodium Laurylsulphate | 0.50% |
| 6 | | Magnesium Stearate | 1.00% |
| 7 | B | Flavor (e.g. 134229 Optamint Peppermint s/d) | 2.00% |
| 8 | | Probiotic Material | 6.67% |
| 9 | C | Calcium Carbonate | 17.00% |
| 10 | | Microcristalline Cellulose | 66.98% |
| | | Sum total | 100.00% |

Production Method:
  components 6, 9 and 10 are dried in a vacuum compartment drier at 50° C. and a pressure of max. 10 mbar for 16 hours.
  all components are weight out exactly
  components 1, 2, 3, 4, 5 and 6 are combined and thoroughly mixed together (block A)
  components 7 and 8 are combined and thoroughly mixed together (block B). The probiotic material is applied in lyophilized form having an activity of about $10^5$ to $10^{12}$ colony forming units (CFU) per gram.
  blocks A and B are subsequently combined and thoroughly mixed together
  components 9 and 10 are combined and thoroughly mixed together (block C)
  the two mixtures (Block A/B and Block C) are combined and mixed thoroughly for 5 minutes
  the powder mixture is pressed into tablets in a tablet press EK0 (Korsch AG, Berlin) at an adjusted pressure of 15-20 kN target parameters
    tablet diameter: 9 mm
    tablet weight: 0.3 g
  storage at RT in sealed aluminum sachets. Per 3 tablets 1 g of desiccant is used for dehumidification (activated by 3 h storage at 105° C. in a vacuum compartment drier)

EXAMPLE 5: CHEWING GUM

| No | Ingredients | Chewing gum with Vegetable Oil, Probiotics in Flavor | | Chewing gum with Vegetable Oil, Probiotics in Oil | |
|---|---|---|---|---|---|
| 1 | Gum Base (e.g. Geminis T) | 30.00% | Block A | 30.00% | Block A |
| 2 | Isomalt (here: Isomalt ST-PF) | 65.00% | Block B | 65.00% | Block B |
| 3 | Sucralose coated (10% in wax) | 1.00% | | 1.00% | |
| 4 | Deoiled Soy Lecithin (here: Emulpur IP) | 0.30% | | 0.30% | |
| 5 | Vegetable Oil - Triglyceride | 1.60% | Block C | 1.60% | Block C |
| 6 | Probiotic Material | 0.80% | Block D | 0.80% | |
| 7 | Flavor (e.g. 203191 Optamint Peppermint) | 1.30% | | 1.30% | Block D |

Production Method:

- component 2 is dried in a vacuum compartment drier at 50° C. and a pressure of max. 10 mbar for 16 hours
- all components are weight out exactly
- component 1 is tempered to 45-59° C. in a chewing gum lab-kneader with the heating kneaded until a homogenous mass is obtained. The heating is on during the whole mixing process
- components 2, 3 and 4 are added subsequently and kneaded until the mixture is homogenous and no powder is visible anymore
- according to the formula component 6 is either worked into component 5 (block C) or component 7 (block D). The probiotic material is applied in lyophilized form having an activity of about $10^5$ to $10^{12}$ colony forming units (CFU) per gram. The components are mixed until an even suspension is obtained.
- First, block C is added to the chewing gum mass and kneaded again until a homogenous mass is obtained.
- Last, block D is processed accordingly. After addition the composition has to be kneaded until an even chewing gum mass is obtained.
- the mass is taken out of the mixer and is formed into mini-sticks by an embossing roller using the embossing set "slabs"
- storage at RT in sealed aluminum sachets. Per 7 chewing gums 1 g of desiccant is used for dehumidification (activated by 3 h storage at 105° C. in a vacuum compartment drier)

EXAMPLE 6: PROBIOTIC BEADLETS

| components | probiotic beadlets with low load, without aroma, with dye, with gellan gum wt. % | probiotic beadlets with low load, with aroma, with dye, with gellan gum wt. % | probiotic beadlets with high load, without aroma, without dye, without gellan gum, high water content wt. % | probiotic beadlets with high load, without aroma without dye, without gellan gum, low water content wt. % |
|---|---|---|---|---|
| Alginate | 1.75 | 1.65 | 1.44 | 1.57 |
| Gummi Arabicum | 1.25 | 1.18 | 0.60 | 0.65 |
| Wheat fiber | 1.125 | 1.06 | 0.52 | 0.57 |
| Dye | 0.0125 | 0.018 | — | — |
| Aroma | — | 1.41 | — | — |
| Glycerol | 0.1875 | — | — | — |
| probiotic | 1.125 | 1.35 | 7.20 | 7.83 |
| Gellan Gum | 0.0625 | 0.059 | — | — |
| Water | Add to 100 | Add to 100 | Add to 100 | Add to 100 |
| load | approx. 20% | approx. 20% | approx. 74% | approx. 74% |

Production Method:

Production of the calcium chloride bath for precipitation of the alginate beadlets:

- a 2% calcium chloride solution is produces from distilled water and calcium chloride. Care has to be taken that the $CaCl_2$ is completely dissolved.
  - Production of the alginate solution (instead of alginate also pectin or gellan gum may be used):
- in a reaction vessel with a stirrer and which is suitable to the batch size, water is provided
- the stirrer is turned on and, while stirring at a high level, the respective amounts of alginate, gum *arabicum*, wheat fiber and probiotic, as well as the optionally required gellan gum are added
- the mixture is heated to 80° C. while stirring and kept at this temperature for 5 minutes—during this step the gel forming components are dissolved
- afterwards, the heating is turned off and the hot gel solution is further stirred for at least 30 minutes until it is free of lumps
- subsequently, the solution is cooled by refrigeration to 39-43° C. while stirring
- in a further vessel, the aroma and the dye are provided if required and thoroughly mixed In case no aroma is used, the dye is mixed with glycerol
- when the dye dispersion is mixed homogenously, it is added to the batch vessel with the alginate solution. The mixing vessel is washed several times with approx. 10% of the amount of alginate solution used of water and added to the dispersion
- the alginate dispersion is stirred further for at least 5 minutes.
- Subsequently, the batch is stirred for further at least 15 minutes at a low speed to remove potentially present air.

Dripping of the Alginate Solution into the Calcium Chloride Solution for Precipitation of the Beadlets:

- the alginate dispersion is moved to a tightly sealable pressure stable reaction vessel having two outlets. At one outlet pressurized air is applied. The second outlet leads to the nozzles of the dripping unit via a tube.
- the reaction vessel is tempered over a heating plate so that the alginate solution reaches a temperature of approx. 45° C. The solution is slightly stirred with a magnet stirrer.
- after application of pressure to the reaction vessel, alginate solution is pressed towards the nozzles, which are set to oscillation by an oscillator. By adaption of pressure and the frequency of the oscillator, the size of the resulting drops at the tips of nozzles may be adjusted.
- The drops of alginate solution forming at the tips of the nozzles fall into a collection vessel in the form of a funnel in which the calcium chloride solution prepared at the beginning circulates.
- the cured alginate beadlets pass with the calcium chloride solution through the funnel and are collected in a sieve, the collected calcium chloride solution is pumped back into the funnel below the dripping unit and thus recycled.
- the beadlets are dried in an Aeromatic flowbed-drier at an supply air temperature of 80° C. until an exhaust air temperature of 45° C. is reached.

REFERENCES 1. van Essche M, Loozen G, Godts C, Boon N, Pauwels M, et al. (2013) Bacterial antagonism against periodontopathogens. J Periodontol 84: 801-811. doi:10.1902/jop.2012.120261.
2. Nyvad B, Fejerskov O (1987) Scanning electron microscopy of early microbial colonization of human enamel and root surfaces in vivo. Scand J Dent Res 95: 287-296.
3. Dewhirst F E, Chen T, Izard J, Paster B J, Tanner A C, et al. (2010) The Human Oral Microbiome. J Bacteriol. doi:10.1128/JB.00542-10.
4. Griffen A L, Beall C J, Campbell J H, Firestone N D, Kumar P S, et al. (2012) Distinct and complex bacterial profiles in human periodontitis and health revealed by 16S pyrosequencing. Isme J 6: 1176-1185. doi:10.1038/ismej.2011.191.
5. Abusleme L, Dupuy A K, Dutzan N, Silva N, Burleson J A, et al. (2013) The subgingival microbiome in health and periodontitis and its relationship with community biomass and inflammation. Isme J 7: 1016-1025. doi:10.1038/ismej.2012.174.
6. Kistler J O, Booth V, Bradshaw D J, Wade W G (2013) Bacterial community development in experimental gingivitis. PLoS ONE 8: e71227. doi:10.1371/journal.pone.0071227.
7. Kinniment S L, Wimpenny J, Adams D, Marsh P D (1996) The effect of chlorhexidine on defined, mixed culture oral biofilms grown in a novel model system. J Appl Bacteriol 81: 120-125.
8. Bradshaw D J, Marsh P D, Schilling K M, Cummins D (1996) A modified chemostat system to study the ecology of oral biofilms. J Appl Bacteriol 80: 124-130.
9. Guggenheim B, Giertsen E, Schupbach P, Shapiro S (2001) Validation of an in vitro biofilm model of supragingival plaque. J Dent Res 80: 363-370.
10. Ceri H, Olson M E, Stremick C, Read R R, Morck D, et al. (1999) The Calgary Biofilm Device: New technology for rapid determination of antibiotic susceptibilities of bacterial biofilms. J Clin Microbiol 37: 1771-1776.
11. Ali L, Khambaty F, Diachenko G (2006) Investigating the suitability of the Calgary Biofilm Device for assessing the antimicrobial efficacy of new agents. Bioresour Technol 97: 1887-1893. doi:10.1016/j.biortech.2005.08.025.
12. Kistler J O, Pesaro M, Wade W G (2015) Development and pyrosequencing analysis of an in-vitro oral biofilm model. BMC Microbiol 15: 364. doi:10.1186/s12866-015-0364-1.
13. Madhwani T, McBain A J (2011) Bacteriological effects of a *Lactobacillus reuteri* probiotic on in vitro oral biofilms. Arch Oral Biol 56: 1264-1273. doi:10.1016/j.archoralbio.2011.04.004.
14. Nocker A, Sossa-Fernandez P, Burr M D, Camper A K (2007) Use of propidium monoazide for live/dead distinction in microbial ecology. Appl Environ Microbiol 73: 5111-5117. doi:10.1128/AEM.02987-06.
15. Frank J A, Reich C I, Sharma S, Weisbaum J S, Wilson B A, et al. (2008) Critical evaluation of two primers commonly used for amplification of bacterial 16S rRNA genes. Appl Environ Microbiol 74: 2461-2470. doi:10.1128/AEM.02272-07.
16. Lane D J, Pace B, Olsen G J, Stahl D A, Sogin M L, et al. (1985) Rapid determination of 16S ribosomal RNA sequences for phylogenetic analyses. Proc Natl Acad Sci USA 82: 6955-6959.
17. Schloss P D, Westcott S L, Ryabin T, Hall J R, Hartmann M, et al. (2009) Introducing mothur: open-source, platform-independent, community-supported software for describing and comparing microbial communities. Appl Environ Microbiol 75: 7537-7541. doi:10.1128/AEM.01541-09.
18. Schloss P D, Westcott S L (2011) Assessing and improving methods used in operational taxonomic unit-based approaches for 16S rRNA gene sequence analysis. Appl Environ Microbiol 77: 3219-3226. doi:10.1128/AEM.02810-10.
19. Quince C, Lanzen A, Davenport R J, Turnbaugh P J (2011) Removing noise from pyrosequenced amplicons. BMC Bioinformatics 12: 38. doi:10.1186/1471-2105-12-38.
20. Pruesse E, Quast C, Knittel K, Fuchs B M, Ludwig W, et al. (2007) SILVA: a comprehensive online resource for quality checked and aligned ribosomal RNA sequence data compatible with ARB. Nucleic Acids Res 35: 7188-7196. doi:10.1093/nar/gkm864.
21. Edgar R C, Haas B J, Clemente J C, Quince C, Knight R (2011) UCHIME improves sensitivity and speed of chimera detection. Bioinformatics 27: 2194-2200. doi:10.1093/bioinformatics/btr381.
22. Wang Q, Garrity G M, Tiedje J M, Cole J R (2007) Naive Bayesian classifier for rapid assignment of rRNA sequences into the new bacterial taxonomy. Appl Environ Microbiol 73: 5261-5267. doi:10.1128/Aem.00062-07.
23. Good I J (1953) The Population Frequencies of Species and the Estimation of Population Parameters. Biometrika 40: 237-264.
24. Simpson E H (1949) Measurement of Diversity. Nature 163: 688-688.
25. Yue J C, Clayton M K (2005) A similarity measure based on species proportions. Commun Stat-Theor M 34: 2123-2131. doi:10.1080/Sta-200066418.
26. Excoffier L, Smouse P E, Quattro J M (1992) Analysis of molecular variance inferred from metric distances among DNA haplotypes: application to human mitochondrial DNA restriction data. Genetics 131: 479-491.
27. Segata N, Izard J, Waldron L, Gevers D, Miropolsky L, et al. (2011) Metagenomic biomarker discovery and explanation. Genome Biol 12: R60. doi:10.1186/gb-2011-12-6-r60.
28. Loe H, Theilade E, Jensen S B (1965) Experimental Gingivitis in Man. J Periodontol 36: 177-187.
29. Moore W E, Holdeman L V, Smibert R M, Good I J, Burmeister J A, et al. (1982) Bacteriology of experimental gingivitis in young adult humans. Infect Immun 38: 651-667.
30. Diaz P I, Chalmers N I, Rickard A H, Kong C, Milburn C L, et al. (2006) Molecular characterization of subject-specific oral microflora during initial colonization of enamel. Appl Environ Microbiol 72: 2837-2848. doi:10.1128/AEM.72.4.2837-2848.2006.
31. Kolenbrander P E, Palmer R J J, Rickard A H, Jakubovics N S, Chalmers N I, et al. (2006) Bacterial interactions and successions during plaque development. Periodontol 2000 42: 47-79. doi:10.1111/j.1600-0757.2006.00187.x.

The invention claimed is:

1. A method of treating periodontal disease in a subject in need thereof, comprising introduction of an effective amount of a microorganism into an oral cavity of the subject to treat periodontal disease, wherein the microorganism is *Lactobacillus paracasei* LPc-G110 (CCTCC M 2013691).

2. The method of claim 1, wherein the microorganism is an attenuated or a dead microorganism.

3. The method of claim 1, wherein the microorganism is a probiotic agent that alters oral biofilms formed by bacteria derived from saliva.

4. The method of claim 1, wherein the method reduces proportions of one or more bacteria selected from the group consisting of Bacteroidetes, *Fusobacterium, Prevotella* and Pyramidobacter; and/or the method increases proportions of *Corynebacterium* and/or *Neisseria*.

5. The method according to claim 1, wherein *Lactobacillus paracasei* LPc-G110 is administered in an amount from $1 \times 10^5$ to $1 \times 10^{10}$ colony forming units (CFU).

6. A method of treating periodontal disease in a subject in need thereof, comprising introduction of a composition or a product into an oral cavity of the subject, wherein the composition or the product comprises *Lactobacillus para-*

*casei* LPc-G110 (CCTCC M 2013691), wherein the total amount of *Lactobacillus paracasei* LPc-G110 (CCTCC M 2013691) is sufficient for treating periodontal disease.

7. The method of claim 6, wherein the method reduces proportions of Gram-negative anaerobic genera; and/or the method increases proportions of aerobic or facultatively anaerobic genera.

8. The method of claim 6, wherein the method reduces proportions of one or more bacteria selected from the group consisting of Bacteroidetes, *Fusobacterium, Prevotella*, and Pyramidobacter; and/or the method increases proportions of *Corynebacterium* and/or *Neisseria*.

9. The method according to claim 6, wherein *Lactobacillus paracasei* LPc-a110 (CCTCC M 2013691) is the only microorganism present in the composition or the product.

10. A method of decreasing the probability for developing periodontal disease in a subject in need thereof, comprising introduction of an effective amount of a microorganism into an oral cavity of the subject to decrease the probability for developing periodontal disease, wherein the microorganism is *Lactobacillus paracasei* LPc-G110 (CCTCC M 2013691); and wherein the microorganism is an attenuated or a dead microorganism.

11. The method of claim 10, wherein the microorganism is a probiotic agent that alters oral biofilms formed by bacteria derived from saliva.

12. The method of claim 10, wherein the method reduces proportions of one or more bacteria selected from the group consisting of Bacteroidetes, *Fusobacterium, Prevotella* and Pyramidobacter; and/or the method increases proportions of *Corynebacterium* and/or *Neisseria*.

13. The method according to claim 10, wherein *Lactobacillus paracasei* LPc-G110 is administered in an amount from $1\times10^5$ to $1\times10^{10}$ colony forming units (CFU).

14. A method of decreasing the probability for developing periodontal disease in a subject in need thereof, comprising introduction of a composition or a product into an oral cavity of the subject, wherein the composition or the product comprises *Lactobacillus paracasei* LPc-G110 (CCTCC M 2013691), wherein the total amount of *Lactobacillus paracasei* LPc-G110 (CCTCC M 2013691) is sufficient for decreasing the probability for developing periodontal disease; and wherein the microorganism is an attenuated or a dead microorganism.

15. The method of claim 14, wherein the method reduces proportions of Gram-negative anaerobic genera; and/or the method increases proportions of aerobic or facultatively anaerobic genera.

16. The method of claim 14, wherein the method reduces proportions of one or more bacteria selected from the group consisting of Bacteroidetes, *Fusobacterium, Prevotella*, and Pyramidobacter; and/or the method increases proportions of *Corynebacterium* and/or *Neisseria*.

17. The method according to claim 14, wherein the *Lactobacillus paracasei* LPc-G110 (CCTCC M 2013691) is the only microorganism present in the composition or the product.

* * * * *